(12) United States Patent
Christopher et al.

(10) Patent No.: US 11,266,384 B2
(45) Date of Patent: Mar. 8, 2022

(54) ERGONOMIC HANDPIECE

(71) Applicant: Johnson & Johnson Surgical Vision, Inc., Santa Ana, CA (US)

(72) Inventors: Stephen M. Christopher, Philadelphia, PA (US); Jacob S. Childs, Huntington Beach, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 82 days.

(21) Appl. No.: 16/386,194

(22) Filed: Apr. 16, 2019

(65) Prior Publication Data
US 2019/0321017 A1    Oct. 24, 2019

Related U.S. Application Data

(60) Provisional application No. 62/660,647, filed on Apr. 20, 2018.

(51) Int. Cl.
*A61B 17/00*    (2006.01)
*A61F 9/007*    (2006.01)
*A61L 31/06*    (2006.01)

(52) U.S. Cl.
CPC .......... *A61B 17/00* (2013.01); *A61F 9/00745* (2013.01); *A61L 31/06* (2013.01); *A61B 2017/00424* (2013.01); *A61B 2017/00477* (2013.01)

(58) Field of Classification Search
CPC .......... A61B 17/00; A61B 2017/00477; A61B 2017/00424; A61F 9/00745; A61L 31/06
See application file for complete search history.

(56) References Cited

U.S. PATENT DOCUMENTS

| | | | |
|---|---|---|---|
| 4,504,264 A | | 3/1985 | Kelman |
| 5,162,044 A | * | 11/1992 | Gahn ................ A61F 9/00745 604/22 |
| 5,413,556 A | * | 5/1995 | Whittingham ...... A61F 9/00745 604/22 |
| 5,453,087 A | * | 9/1995 | Malinowski ........ A61F 9/00745 604/22 |
| 5,609,602 A | | 3/1997 | Machemer et al. |
| 5,653,724 A | * | 8/1997 | Imonti ................ A61F 9/00745 604/22 |
| 5,843,109 A | | 12/1998 | Mehta et al. |
| 6,852,092 B2 | | 2/2005 | Kadziauskas et al. |
| 7,169,123 B2 | | 1/2007 | Kadziauskas et al. |

(Continued)

FOREIGN PATENT DOCUMENTS

| | | |
|---|---|---|
| WO | 2015144890 A1 | 10/2015 |
| WO | 2016172113 A1 | 10/2016 |

OTHER PUBLICATIONS

International Search Report and Written Opinion for Application No. PCT/IB2019/053188, dated Jul. 23, 2019, 13 pages.

*Primary Examiner* — Richard G Louis
(74) *Attorney, Agent, or Firm* — Johnson & Johnson Surgical Vision, Inc.

(57) ABSTRACT

The present invention pertains to a handpiece and more particular an ergonomic handpiece having two or more segments coupled together and capable of independently rotating around a longitudinal axis of the handpiece. In addition, one of the segments of the handpiece may have a tubing/cord management segment.

23 Claims, 10 Drawing Sheets

(56) References Cited

U.S. PATENT DOCUMENTS

| | | | |
|---|---|---|---|
| 2001/0018570 A1* | 8/2001 | Sussman | A61F 9/00736 |
| | | | 604/114 |
| 2006/0079832 A1 | 4/2006 | Akahoshi | |
| 2008/0255579 A1 | 10/2008 | Wollenhaupt et al. | |
| 2011/0009874 A1 | 1/2011 | Wardle et al. | |
| 2012/0078234 A1 | 3/2012 | Merchant et al. | |
| 2016/0331516 A1 | 11/2016 | Novak | |
| 2017/0071787 A1 | 3/2017 | Canelli et al. | |

\* cited by examiner

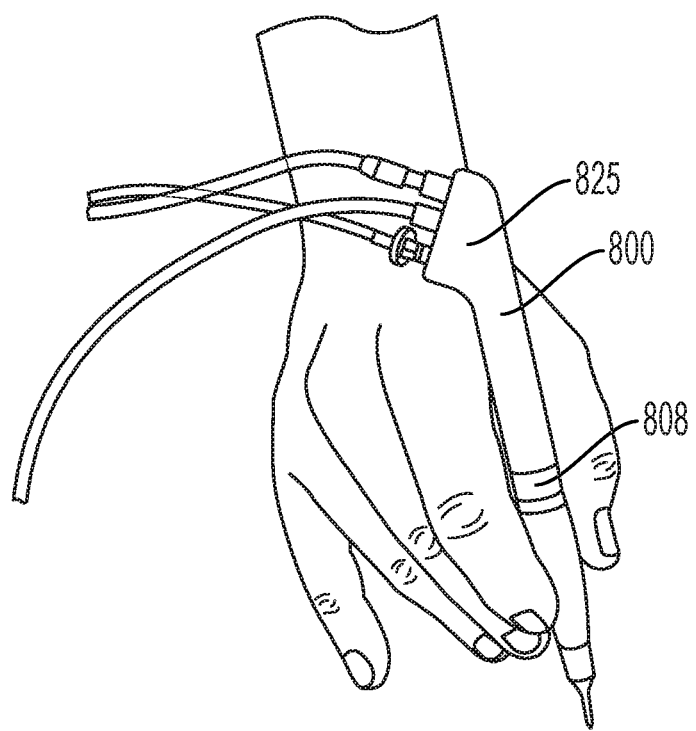

ERGONOMIC HANDPIECE

CROSS REFERENCE TO RELATED APPLICATIONS

This application claims the benefit under 35 U.S.C. § 119(e) of U.S. Provisional Patent Application No. 62/660,647, filed Apr. 20, 2018, which is incorporated herein by reference in its entirety.

FIELD OF THE INVENTION

The field of the invention relates to a handpiece, and more particularly to an apparatus, system and method for ergonomic handpieces.

BACKGROUND OF THE INVENTION

The phacoemulsification method includes emulsifying, or liquefying, the cataractic lens with an ultrasonically driven needle before the lens is aspirated. A phacoemulsification system 5 known in the art is shown in FIG. 1. The system 5 generally includes a phacoemulsification handpiece 10 coupled to an irrigation source 30 an and more or more aspiration pumps, e.g. pump 40. The handpiece 10 includes a distal tip (or needle) 15 (shown within the anterior chamber of the patient's eye 1 that emits ultrasonic energy to emulsify the cataractic lens within the patient's eye 1. The handpiece 10 further includes a sleeve 26 that surrounds at least a portion of needle 15 and has one or more irrigation ports 25 proximal to the distal tip 15, which is coupled to an irrigation source 30 via an irrigation line 35, and an aspiration port 20 at the distal tip 15, which is coupled to an aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractic lens material are aspirated from the eye 1 by the aspiration pump 40 via the aspiration port 20 and the aspiration line 45.

Turning to FIG. 2, a functional block diagram of a phacoemulsification system 100 known in the art is shown. The system 100 includes a control unit 102 and a handpiece 104 operably coupled together. The control unit 102 generally controls the operating parameters of the handpiece 104, e.g., the rate of aspiration A, rate of irrigation (or flow) F, and power P applied to the needle, and hence the eye E. The control unit 102 generally includes a microprocessor computer 110 which is operably connected to and controls the various other elements of the system 100. The control unit 102 may include an aspiration pump, such as a Venturi (or vacuum-based pump) or a variable speed pump (or a flow based or peristaltic pump) 112 for providing a vacuum/aspiration source, which, in the case of a variable speed pump 112, can be controlled by a pump speed controller 116. The unit 102 further includes an ultrasonic power source 114 and an ultrasonic power level controller 118 for controlling the power P applied to the needle of the handpiece 104. A vacuum sensor 120 provides an input to the computer 110 representing the vacuum level on the output side of the pump 112. Venting may be provided by a vent 122. The system 100 may also include a phase detector 124 for providing an input to the computer 100 that represents the phase between a sine wave representation of the voltage applied to the handpiece 104 and the resultant current into the handpiece 104. Further disclosure about the phase detector 124 can be found in U.S. Pat. No. 7,169,123 to Kadziauskas et al., which is incorporated herein in its entirety by reference. The functional representation of the system 100 also includes a system bus 126 to enable the various elements to be operably in communication with each other.

Turning to FIG. 3, the cross-section along the longitudinal axis of a portion of a phacoemulsification handpiece 200 known in the art is shown. Generally, the handpiece 200 includes a needle 210, defining a lumen that is operatively coupled to an aspiration pump (e.g. aspiration pump 40 (FIG. 1)), forming an aspiration line 214. At least a portion of the distal end of needle 210 is surrounded by sleeve 220 and proximal end of the needle 210 is coupled to a horn 250, which has its proximal end coupled to a set of piezoelectric crystals 280, shown as three rings. The horn 250, crystals 280, and a proximal portion of the needle 210 are enclosed within a handpiece casing 270 having an irrigation port coupled to an irrigation line 290 defining an irrigation pathway 295. Irrigation pathway 295 extends between the wall of sleeve 220 and the wall of needle 210 allowing fluid to flow around needle 210 and exit one or more ports 225 in sleeve 220. The irrigation line 290 is coupled to the irrigation source 30 (FIG. 1). The horn 250 is typically an integrated metal, such as titanium, structure and often includes a rubber O ring 260 around the mid-section, just before the horn 250 tapers to fit with the needle 210 at the horn's 250 distal end. The O-ring 260 snugly fits between the horn 250 and the casing 270. The O ring 260 seals the proximal portion of the horn 250 from the irrigation pathway 295. Thus, there is a channel of air defined between the horn 250 and the casing 270. Descriptions of handpieces known in the art are provided in U.S. Pat. No. 6,852,092 (to Kadziauskas et al.) and U.S. Pat. No. 5,843,109 (to Mehta et al.), which are hereby incorporated by reference in their entirety.

In preparation for operation, a sleeve 220 is typically added to the distal end of the handpiece 200, covering the proximal portion of the needle 210 (thus, exposing the distal tip of the needle), and the distal end of the irrigation pathway 295, thereby extending the pathway 295 and defining an irrigation port 222 just before the distal tip of the needle 210. The needle 210 and a portion of the sleeve 220 are then inserted through the cornea of the eye to reach the cataractic lens.

During operation, the irrigation path 295, the eye's chamber and the aspiration line 214 form a fluidic circuit, where irrigation fluid enters the eye's chamber via the irrigation path 295, and is then aspirated through the aspiration line 214 along with other materials that the surgeon desires to aspirate out, such as the cataractic lens. If, however, the materials, such as the cataractic lens, are too hard and massive to be aspirated through the aspiration line 214, then the distal end of the needle 210 is ultrasonically vibrated and applied to the material to be emulsified into a size and state that can be successfully aspirated.

The needle 210 is ultrasonically vibrated by applying electric power to the piezoelectric crystals 280, which in turn, cause the horn 250 to ultrasonically vibrate, which in turn, ultrasonically vibrates the needle 210. The electric power is defined by a number of parameters, such as signal frequency and amplitude, and if the power is applied in pulses, then the parameters can further include pulse width, shape, size, duty cycle, amplitude, and so on. These parameters are controlled by the control unit 102 and example control of these parameters is described in U.S. Pat. No. 7,169,123 to Kadziauskas et al.

With respect to FIG. 4, an exemplary handpiece known in the prior art is shown. As discussed above, the distal end 401 of the handpiece 400 is show with a tip/needle 404 and sleeve 403 having port 405. The proximal end 402 of the of the handpiece 400 comprises multiple ports/connector points 406, include a port 406a for connecting to the irrigation line, a port 406b for connecting to the aspiration line, and a connector port 406c for electrical power for the ultrasound. The location of the ports/connector points 406 at the proximal end 402 of the handpiece 400 are known to create fatigue on the surgeon's hand and wrist due to the orientation of the ports/connector points 406 and the weight of the proximal end 402 once the irrigation and aspiration lines and the power cord are connected to the handpiece (not shown). Also, as shown in FIG. 4, the handpiece is typically one piece made of a metal type material and to adjust or rotate the distal end of the phacoemulsification (phaco) tip/needle requires the entire handpiece and connected lines to be moved/rotated to achieve the desired position. Such requirement of moving/rotating the entire handpiece is also known to create fatigue for the surgeon's hand and/or wrist during surgery. As such, a new ergonomic handpiece with features that address these drawbacks is needed.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIGS. 8a, 8b, and 8c show different orientations of a handpiece of the present invention.

DETAILED DESCRIPTION OF THE INVENTION

The present invention relates to ergonomic handpieces and in particular a handpiece that has one or more moveable segments and/or cord and irrigation/aspiration line management.

Figure 1:
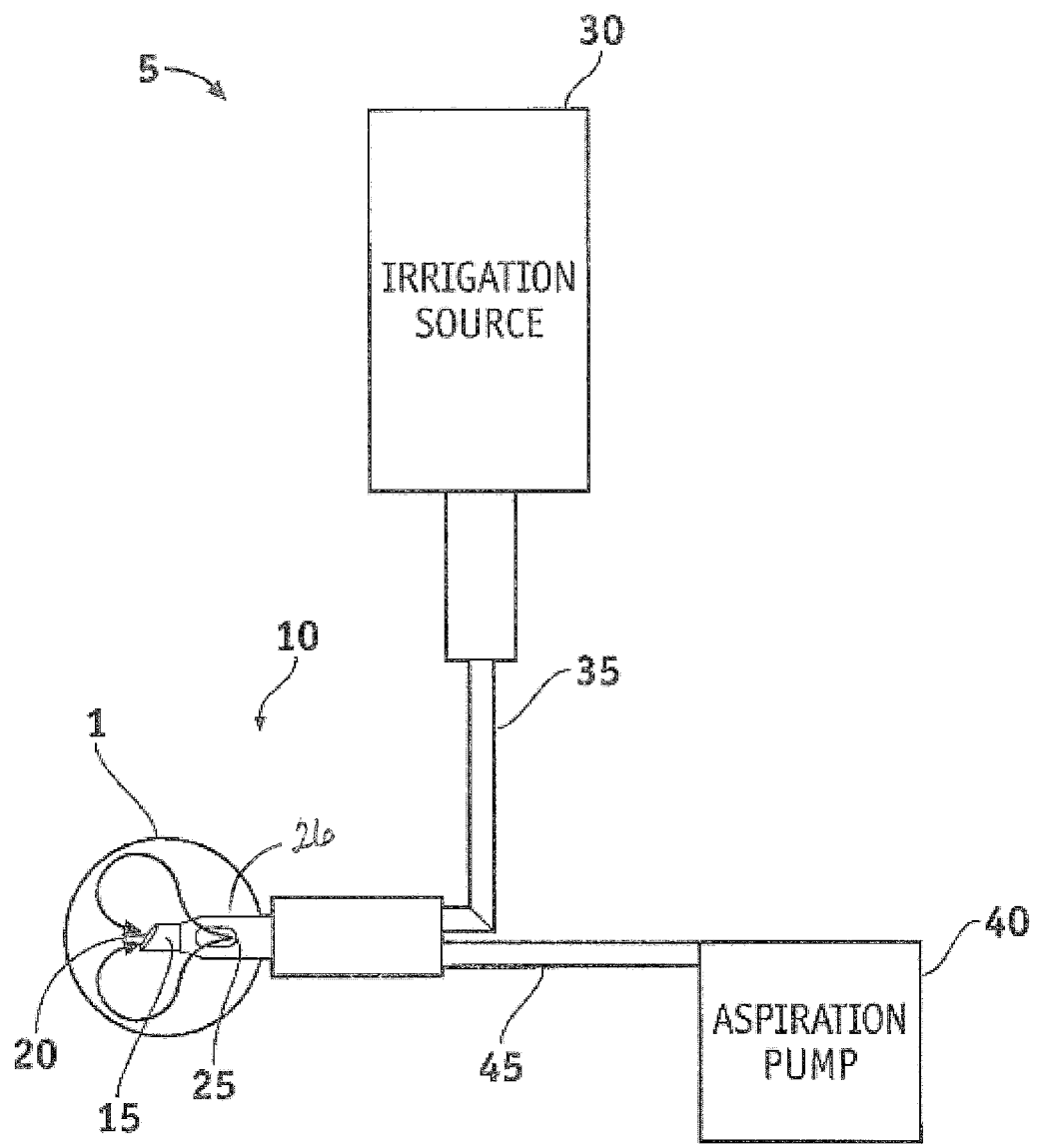
FIG. 1 is a diagram of a phacoemulsification system known in the art.
Figure 2:
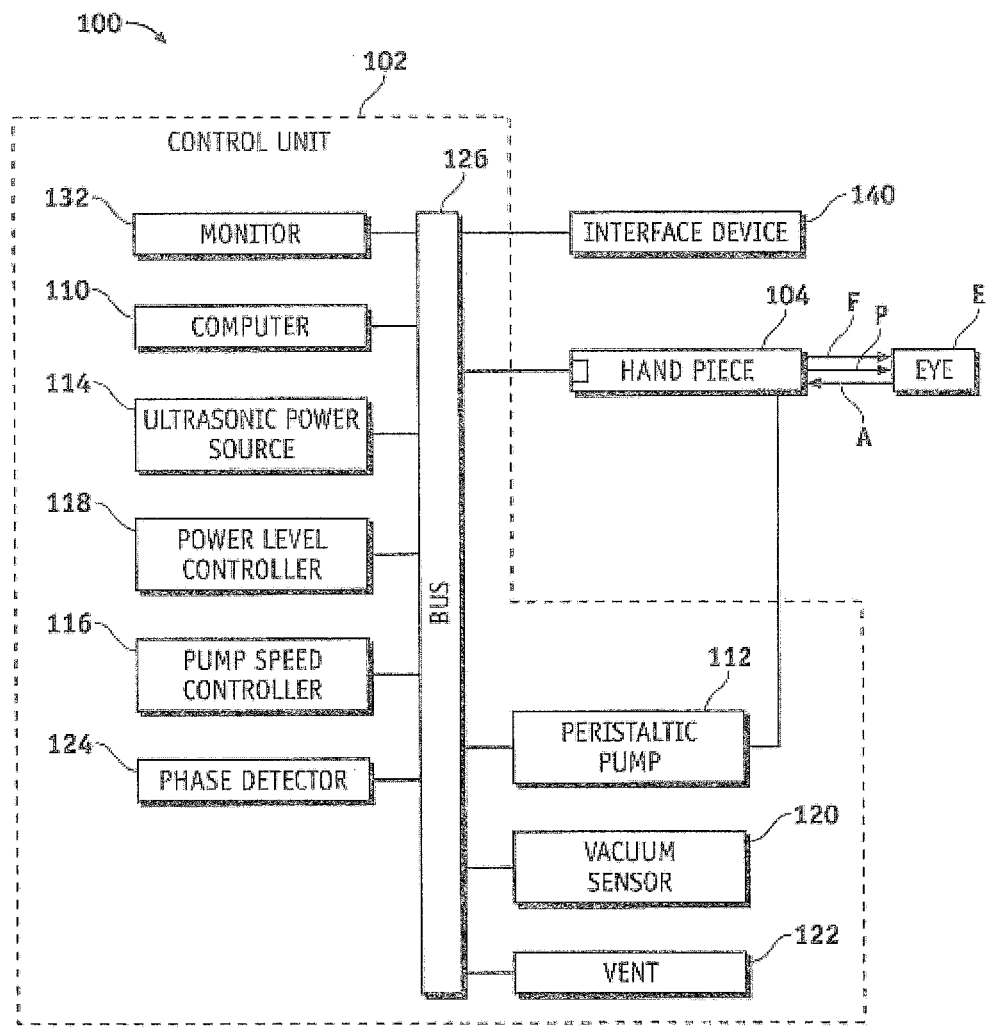
FIG. 2 is another diagram of a phacoemulsification system known in the art.
Figure 3:
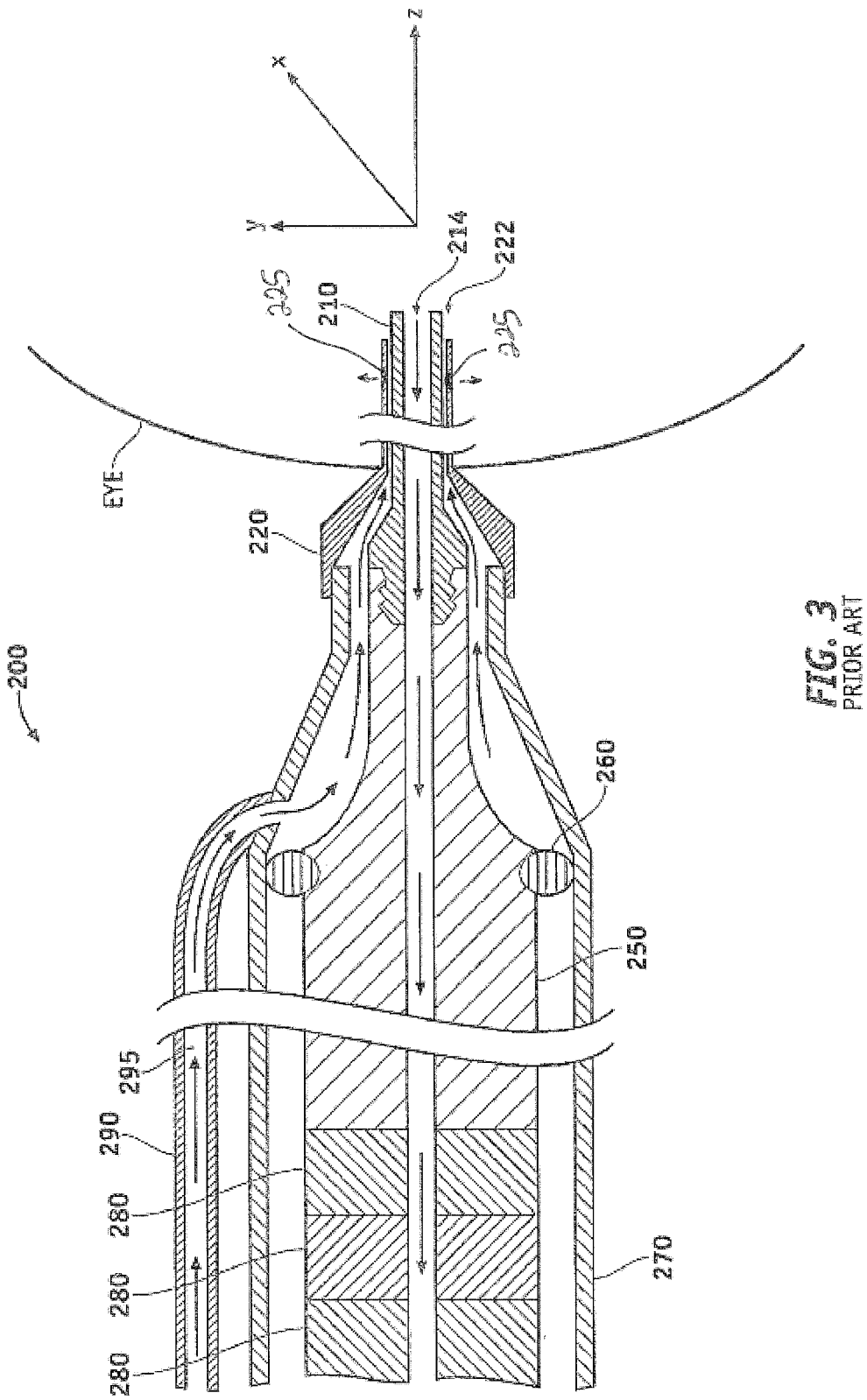
FIG. 3 is a diagram of a phacoemulsification handpiece known in the art.
Figure 4:
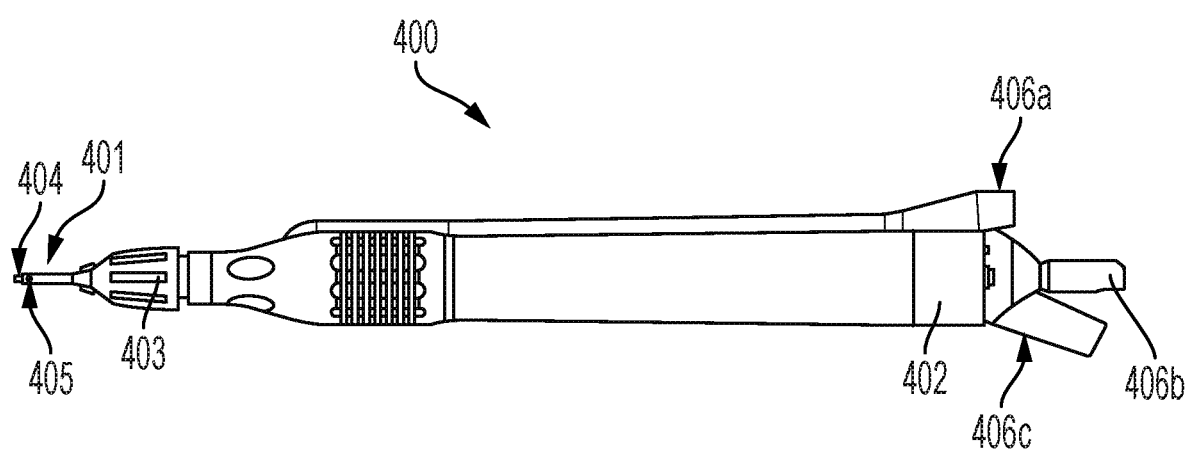
FIG. 4 is an example of a phacoemulsification handpiece known in the art.
Figure 5A:
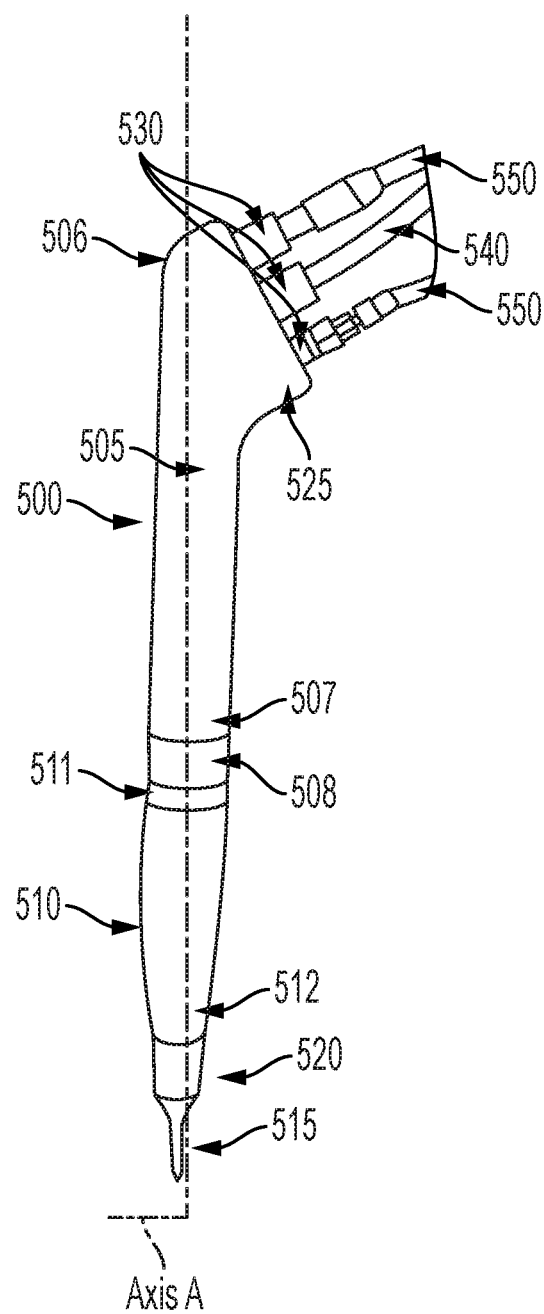
FIGS. 5a and 5b show embodiments of a handpiece of the present invention.

In an embodiment, as shown in FIG. 5, the handpiece 500 may have at least two segments, a proximal segment 505 and a distal segment 510. Proximal segment 505 and distal segment 510 may be referred to as first segment 505 and second segment 510, respectively. Proximal segment 505 and distal segment 510 may be coupled to each other. Proximal segment 505 may have a first end 506 and a second end 507. Distal segment 510 may have a first end 511 and a second end 512. Proximal segment 505 may be coupled to distal segment 510 via the first end 511 and second end 507. First segment 505 and second segment 510 may be coupled together by coupler 508 by any means known in the art, including, but not limited to a snap fit feature having male and female connectors. The male or female connector may be located on the first end 511 and the opposite connector on the second end 507. In addition, at least one coupler 508 may be a part of the proximal segment 505 or the distal segment 510 and have a swivel feature allowing proximal segment 505 and distal segment 510 to rotate along an axis A independently of each other. In an embodiment, the proximal and/or distal segments are capable of rotating 360 degrees. In another embodiment, the rotation may be limited to less than 360 degrees depending upon the freedom of movement and amount of control desired. In an embodiment, the material of the coupler may be the same as the segment it is connected to or may be of a different material.

In an embodiment, the distal segment 510 of handpiece 500 may have a needle 515 connected to a distal portion of distal segment 510. A sleeve 520 may also be coupled with handpiece 500 and at least partial surround needle 515. Needle 515 and sleeve 520 may be separate components attachable to the distal segment 510a or may be integrally coupled with the distal segment 510 of handpiece 500. Proximal segment 505 of handpiece 500 includes tubing/cord management section 525 that includes one or more port/connector 530.

The location and position of the one or more port/connector 530 helps manage the cords 540 and/or tubing 550 connected thereto. It allows the connected cords and/or tubing lay or rest against a user's hand to keep the same in a comfortable and convenient location. The one or more port/connector 530 may all be aligned or may exit the tubing/cord management section 525 at any angle to achieve an ergonomic handpiece. In an embodiment, the port/connector 530 are between 0 degrees and 90 degrees from the longitudinal Axis A, preferably 0 degrees to 45 degrees.

Figure 5B:
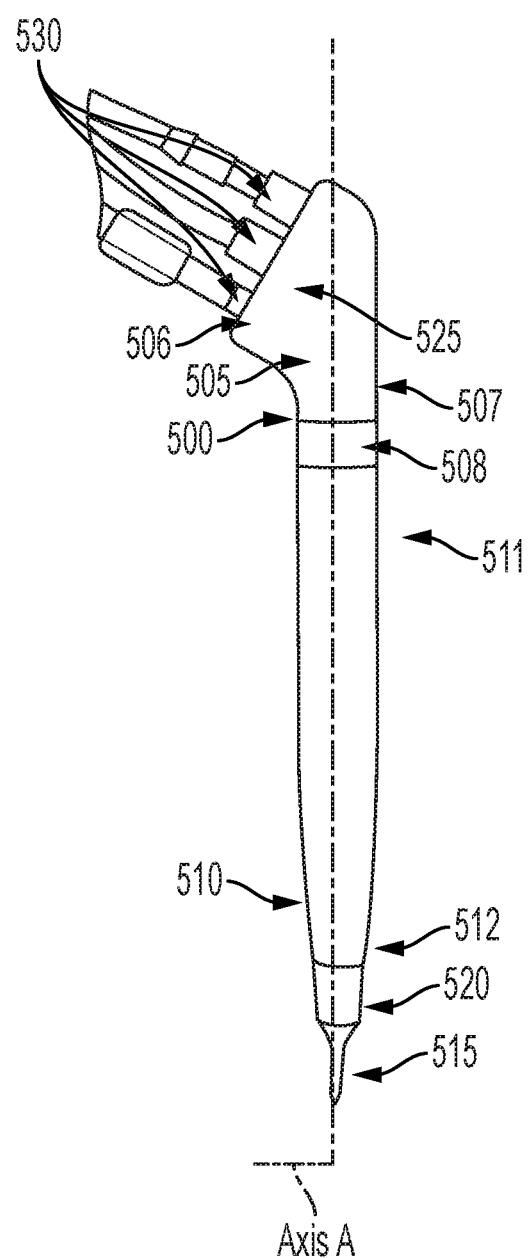

According to an embodiment, a user's hand may grip the first segment 505 with her fingers and rest the second segment 510 on the hand between the thumb and pointer finger. This positioning coupled with a swivel connector allows the user to rotate first segment 505 independent of second segment 510. Second segment 510 may remain stationary. The length of the proximal segment and distal segment may vary to achieve the desired balance of the handpiece. For example, as shown in FIG. 5b, a similar handpiece 500 is shown with similar features having the same corresponding reference numbers as in FIG. 5a, however the length of proximal segment 505 and distal segment 510 are different. Proximal segment 505 is shorter and distal segment 510 is longer. The coupler 508 is now located more proximally on the handpiece 500.

Figure 6:
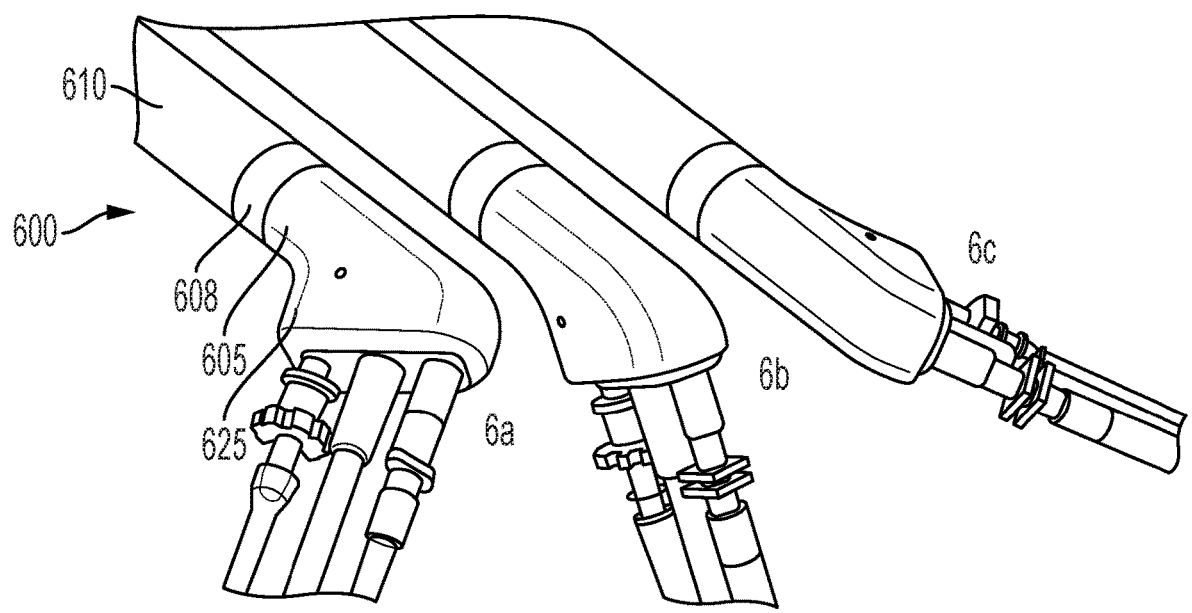
FIG. 6 shows an embodiment of a handpiece of the present invention.

According to an embodiment, in FIG. 6, tubing/cord management section 625 is shown in three different geometries (6a, 6b, and 6c). The tubing/cord management section 625 may achieve the different rotational geometries relative to the rest of the handpiece via coupler 608. In an embodiment the proximal segment 605 primarily includes the tubing/cord management section 625 and the distal segment 610 includes a majority of the length of the handpiece 600.

Figure 7:
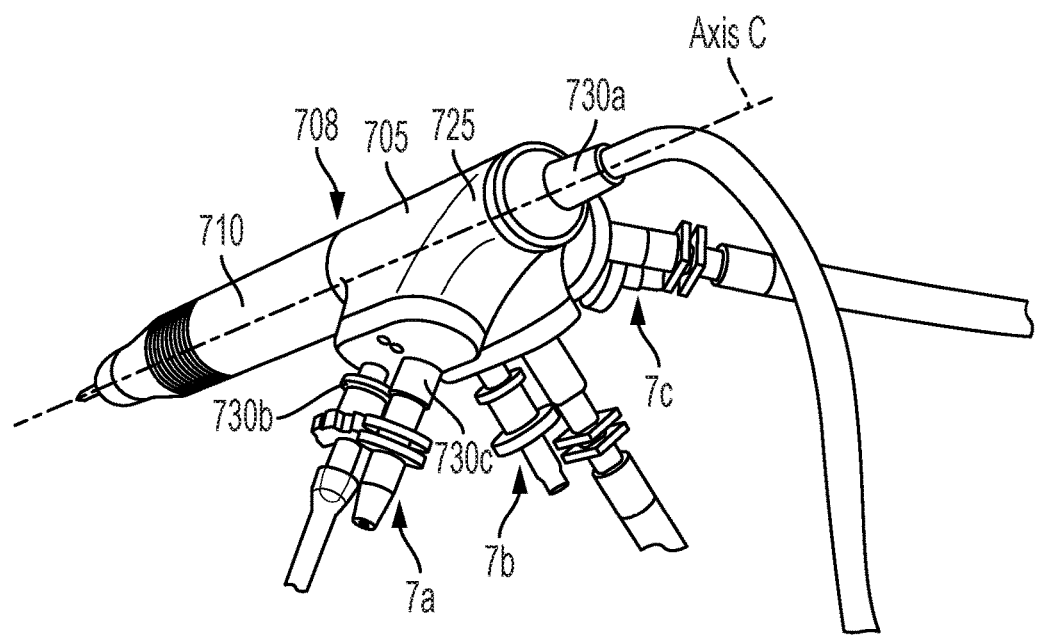
FIG. 7 shows an embodiment of a handpiece of the present invention.

In an embodiment shown in FIG. 7, tubing/cord management section 725 is shown in three different geometries (7a, 7b, 7c), but also with a different orientation for one or more port/connector 730. In the embodiment, the port/connector 730a is in line with Axis C and port connector 730b and 730c are located at an angle from Axis C. Coupler 708 may be part of proximal segment 705 or distal segment 720. Rotation of distal segment 710 around Axis C is possible without movement/rotation of proximal segment 705.

Figure 8B:
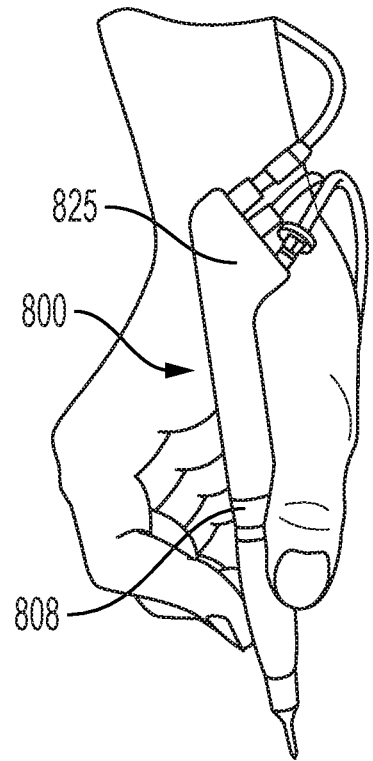
Figure 8C:
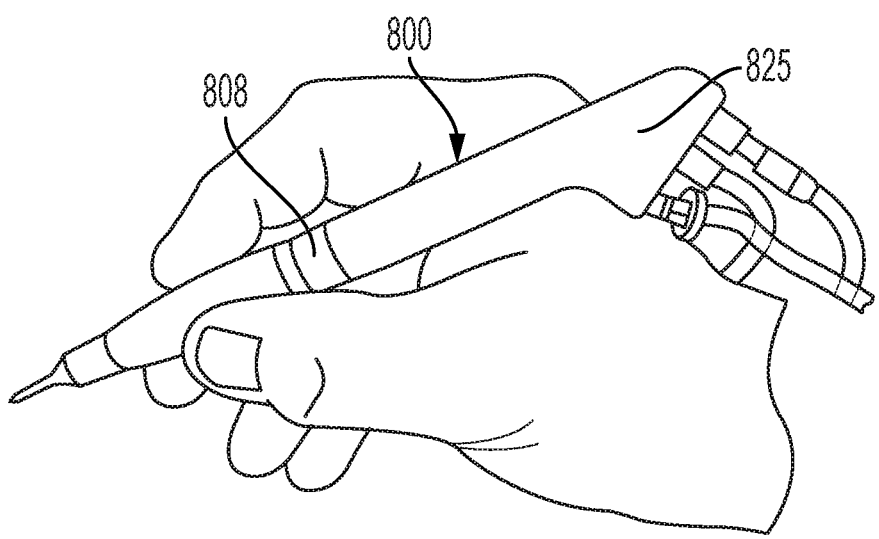

As shown in FIGS. 8a, 8b, and 8c, the tubing/cord management section 825 of handpiece 800 may be placed in multiple orientations depending upon a user's preference. Since handpiece 800 has at least two independently movable segments, e.g. proximal segment 805 and distal segment 810 coupled together via coupler 808 (as shown in FIGS. 8a, 8b, and 8c), tubing/cord management section 825 may remain stationary in the user's desired position while the distal segment 810 may be rotated around the longitudinal axis of the handpiece.

Figure 9:
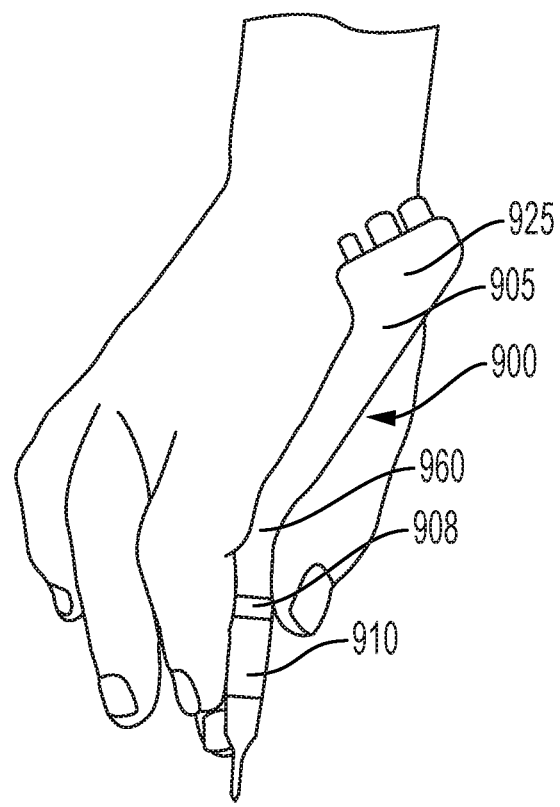
FIG. 9 shows an embodiment of a handpiece of the present invention.

In another embodiment, proximal segment 905 and distal segment 910 may be of any shape, e.g. straight, bent, curved, etc. to assist with the ergonomics of handpiece 900. An example of such a handpiece 900 is shown in FIG. 9, where proximal segment 905 may have a bend or curve 960. In an embodiment, the bend or curve 960 has an angle between 0 degrees and 90 degrees, preferably between 0 degrees and 45 degrees. The bend or curve 960 may be located along any portion of segment 905 and in other embodiments may be located on the distal segment 910. Having such a curve or bend 960 may help achieve an ergonomic feel of handpiece 900 and provide a more comfortable location for tubing/cord management section 925. In addition, in an embodiment coupler 908 may be located on the proximal segment 905, the distal segment 910, or may be a separate component coupled with proximal segment 905 and distal segment 910 and allow each segment to move or rotate independently.

In an embodiment, the internal structures needed for activation of ultrasound for a phacoemulsification handpiece, e.g. piezoelectric crystals, may be located in either the first segment, the second segment, or both. In an embodiment, if there are more than two segments, the various internal structures may be located in any segment or in multiple segments.

In an embodiment, the needle 515 and sleeve 520 may be separate parts used for rotations and are independent of the internal components of the handpiece. In addition, one or more O-ring gaskets may be used on the proximal and distal segments to create a seal between the parts and assist with rotation. In an additional embodiment, bearings or tubing may be used alone or in combination with another similar feature, e.g. O-ring, bearing, tubing, etc., for creating a seal between the various parts of the handpiece to prevent fluids from entering or exiting the handpiece as these locations.

In an embodiment the multiple segment, e.g. the distal segment and proximal segment, may be separable to replace the distal segment with another distal segment that may have the same or different needle and/or sleeve. In addition, the proximal segment may be designed to be serializable and thus, reusable. The distal segment may be designed to be disposable or reusable.

In an embodiment, the one or more segments may be of any material suitable for the handpiece application. The segments may be titanium, plastic, rubber, or any similar material. Each segment may have its own material type or the same material type as another segment.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure.

The invention claimed is:

1. A handpiece comprising: a first segment disposed along a longitudinal axis of the handpiece and comprising a first end, a second end, and a tubing and cord management section located on the first end; and a second segment disposed along the longitudinal axis of the handpiece and comprising a first end and a second end, the first end of the second segment being between the second end of the first segment and the second end of the second segment wherein the second end comprises a needle, wherein the second end of the first segment is coupled with the first end of the second segment and the first segment and the second segment are capable of rotating independently around the longitudinal axis of the handpiece.

2. The handpiece of claim 1, wherein the second end of the first segment is coupled with the first end of the second segment via a coupler.

3. The handpiece of claim 2, wherein the coupler is a portion of the first segment or the second segment.

4. The handpiece of claim 2, wherein the coupler is a separate component coupled with the first segment and the second segment.

5. The handpiece of claim 4, wherein the coupler comprises a swivel element.

6. The handpiece of claim 1, wherein the tubing and cord management section includes at least one port.

7. The handpiece of claim 6, wherein the at least one port exits the tubing and cord management section at an angle.

8. The handpiece of claim 7, wherein the angle is between 0 degrees and 90 degrees from the longitudinal axis of the first segment.

9. The handpiece of claim 7, wherein the angle is between 0 degrees and 45 degrees from the longitudinal axis of the first segment.

10. The handpiece of claim 1, wherein the first segment is longer than the second segment.

11. The handpiece of claim 1, wherein the second segment is longer than the first segment.

12. The handpiece of claim 1, wherein the first segment comprises a curve located along a portion of the first segment.

13. The handpiece of claim 12, wherein the curve has an angle between 0 degrees and 45 degrees.

14. The handpiece of claim 1, wherein the second segment comprises a curve located along a portion of the second segment.

15. The handpiece of claim 14, wherein the curve has an angle between 0 degrees and 45 degrees.

16. The handpiece of claim 1, wherein the handpiece is a phacoemulsification handpiece, and
wherein one or more structures for activation of ultrasound is located inside the first segment, the second segment, or both the first segment and the second segment.

17. The handpiece of claim 1, wherein the first segment is reusable and the second segment is disposable.

18. The handpiece of claim 1, wherein the first segment is separable from the second segment to replace the second segment.

19. The handpiece of claim 1, wherein the first segment and the second segment are each comprised of one of titanium, plastic or rubber.

20. The handpiece of claim 1, wherein the tubing and cord management section of the first section is configured to be placed in the multiple orientations to achieve different rotational geometries relative to a remainder of the handpiece via a coupler, each rotational geometry enabling effective stable and ergonomic contact between the first or second segments and a hand engaged with the handpiece.

21. The handpiece of claim 1, wherein an ergonomic shape of the tubing and cord management section enables the handpiece to lay or rest against a user's hand.

22. The handpiece of claim 1, wherein the tubing and cord management section comprises an ergonomic shape spanning from the longitudinal axis at an angle to enable the handpiece to be placed in the multiple orientations.

23. The handpiece of claim 22, wherein the angle of the ergonomic shape is between 0 degrees and 90 degrees from the longitudinal axis.

* * * * *